(12) United States Patent
Schuman (10) Patent No.: US 7,831,447 B2
(45) Date of Patent: *Nov. 9, 2010

(54) HEALTHCARE COMPUTER SYSTEM

(75) Inventor: Richard J. Schuman, Cary, NC (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/757,072

(22) Filed: Apr. 9, 2010

(65) Prior Publication Data

US 2010/0191543 A1    Jul. 29, 2010

Related U.S. Application Data

(63) Continuation of application No. 11/959,660, filed on Dec. 19, 2007, now Pat. No. 7,715,387, which is a continuation of application No. 11/330,021, filed on Jan. 11, 2006, now Pat. No. 7,315,535, which is a continuation of application No. 10/114,682, filed on Apr. 1, 2002, now Pat. No. 7,092,376.

(60) Provisional application No. 60/280,002, filed on Mar. 30, 2001.

(51) Int. Cl.
*G06Q 10/00* (2006.01)
*G06F 19/00* (2006.01)

(52) U.S. Cl. ............................................. 705/2; 705/3

(58) Field of Classification Search ................. 705/2–3
See application file for complete search history.

(56) References Cited

U.S. PATENT DOCUMENTS

| | | | |
|---|---|---|---|
| 3,439,320 A | 4/1969 | Ward | |
| 3,617,637 A | 11/1971 | Gorman, II | |
| 3,696,384 A | 10/1972 | Lester | |
| 3,739,329 A | 6/1973 | Lester | |
| 3,767,859 A | 10/1973 | Doering et al. | |
| 3,805,227 A | 4/1974 | Lester | |
| 3,805,265 A | 4/1974 | Lester | |
| 3,816,662 A | 6/1974 | Shaver et al. | |
| 3,872,440 A | 3/1975 | Benz et al. | |
| 3,925,762 A | 12/1975 | Heitlinger et al. | |
| 3,946,159 A | 3/1976 | Fay | |
| 3,971,916 A | 7/1976 | Moreno | |
| 4,126,768 A | 11/1978 | Grenzow | |
| 4,135,241 A | 1/1979 | Stanis et al. | |

(Continued)

FOREIGN PATENT DOCUMENTS

CA    2091393    3/1999

(Continued)

OTHER PUBLICATIONS

J H. U. Brown et al., "A new Patient Record System Using the LaserCard", Optical Information Systems, Jul.-Aug. 1988.

(Continued)

*Primary Examiner*—Robert W Morgan
(74) *Attorney, Agent, or Firm*—Barnes & Thornburg LLP (57) ABSTRACT

A hospital bed, patient/nurse call system, and a hospital network are provided. Communication is provided over a packet based communication network.

20 Claims, 8 Drawing Sheets

U.S. PATENT DOCUMENTS

| | | | |
|---|---|---|---|
| 4,151,407 A | 4/1979 | McBride et al. |
| 4,183,015 A | 1/1980 | Drew et al. |
| 4,216,462 A | 8/1980 | McGrath et al. |
| 4,225,953 A | 9/1980 | Simon et al. |
| 4,237,344 A | 12/1980 | Moore |
| 4,275,266 A | 6/1981 | Lasar |
| 4,275,385 A | 6/1981 | White |
| 4,356,475 A | 10/1982 | Neumann et al. |
| 4,401,852 A | 8/1983 | Noso et al. |
| 4,410,883 A | 10/1983 | Swiston, Sr. |
| 4,435,862 A | 3/1984 | King et al. |
| 4,463,352 A | 7/1984 | Forbes et al. |
| 4,491,947 A | 1/1985 | Frank |
| 4,520,576 A | 6/1985 | Vander Molen |
| 4,536,646 A | 8/1985 | Adams et al. |
| 4,553,267 A | 11/1985 | Crimmins |
| 4,577,060 A | 3/1986 | Webb et al. |
| 4,601,064 A | 7/1986 | Shipley |
| 4,648,123 A | 3/1987 | Schrock |
| 4,649,385 A | 3/1987 | Aires et al. |
| 4,680,785 A | 7/1987 | Akiyama et al. |
| 4,680,790 A | 7/1987 | Packard et al. |
| 4,752,951 A | 6/1988 | Konneker |
| 4,757,553 A | 7/1988 | Crimmins |
| 4,807,155 A | 2/1989 | Cree et al. |
| 4,814,751 A | 3/1989 | Hawkins et al. |
| 4,835,372 A | 5/1989 | Gombrich et al. |
| 4,837,568 A | 6/1989 | Snaper |
| 4,838,275 A | 6/1989 | Lee |
| 4,850,040 A | 7/1989 | Teich et al. |
| 4,853,692 A | 8/1989 | Wolk et al. |
| 4,899,334 A | 2/1990 | Shimizu |
| 4,899,373 A | 2/1990 | Lee et al. |
| 4,905,231 A | 2/1990 | Leung et al. |
| 4,940,963 A | 7/1990 | Gutman et al. |
| 4,955,000 A | 9/1990 | Nastrom |
| 4,955,019 A | 9/1990 | Mizuhara et al. |
| 4,967,195 A | 10/1990 | Shipley |
| 4,968,966 A | 11/1990 | Jasinski et al. |
| 4,977,619 A | 12/1990 | Crimmins |
| 4,990,892 A | 2/1991 | Guest et al. |
| 5,003,984 A | 4/1991 | Muraki et al. |
| 5,027,314 A | 6/1991 | Linwood et al. |
| 5,036,852 A | 8/1991 | Leishman |
| 5,051,741 A | 9/1991 | Wesby |
| 5,051,924 A | 9/1991 | Bergeron et al. |
| 5,054,052 A | 10/1991 | Nonami |
| 5,062,151 A | 10/1991 | Shipley |
| 5,065,315 A | 11/1991 | Garcia |
| 5,077,666 A | 12/1991 | Brimm et al. |
| 5,101,476 A | 3/1992 | Kukla |
| 5,119,104 A | 6/1992 | Heller |
| 5,121,384 A | 6/1992 | Ozeki et al. |
| 5,127,003 A | 6/1992 | Doll, Jr. et al. |
| 5,130,793 A | 7/1992 | Bordry et al. |
| 5,140,626 A | 8/1992 | Ory et al. |
| 5,148,148 A | 9/1992 | Shima et al. |
| 5,153,584 A | 10/1992 | Engira |
| 5,204,670 A | 4/1993 | Stinton |
| 5,218,344 A | 6/1993 | Ricketts |
| 5,227,776 A | 7/1993 | Starefoss |
| 5,228,449 A | 7/1993 | Christ et al. |
| 5,239,300 A | 8/1993 | Berger et al. |
| 5,262,944 A | 11/1993 | Weisner et al. |
| 5,274,311 A | 12/1993 | Littlejohn et al. |
| 5,276,813 A | 1/1994 | Elliott et al. |
| 5,283,781 A | 2/1994 | Buda et al. |
| 5,291,399 A | 3/1994 | Chaco |
| 5,301,105 A | 4/1994 | Cummings, Jr. |
| 5,317,309 A | 5/1994 | Vercellotti et al. |
| 5,319,363 A | 6/1994 | Welch et al. |
| 5,323,384 A | 6/1994 | Norwood et al. |
| 5,335,313 A | 8/1994 | Douglas |
| 5,345,226 A | 9/1994 | Rice, Jr. et al. |
| 5,363,425 A | 11/1994 | Mufti et al. |
| 5,387,993 A | 2/1995 | Heller et al. |
| 5,390,238 A | 2/1995 | Kirk et al. |
| 5,394,882 A | 3/1995 | Mawhinney |
| 5,396,224 A | 3/1995 | Dukes et al. |
| 5,402,469 A | 3/1995 | Hopper et al. |
| 5,417,222 A | 5/1995 | Dempsey et al. |
| 5,426,425 A | 6/1995 | Conrad et al. |
| RE35,035 E | 9/1995 | Shipley |
| 5,455,851 A | 10/1995 | Chaco et al. |
| 5,458,123 A | 10/1995 | Unger |
| 5,465,082 A | 11/1995 | Chaco |
| 5,471,404 A | 11/1995 | Mazer |
| 5,473,667 A | 12/1995 | Neustein |
| 5,493,283 A | 2/1996 | Hopper et al. |
| 5,511,553 A | 4/1996 | Segalowitz |
| 5,515,426 A | 5/1996 | Yacenda et al. |
| 5,534,851 A | 7/1996 | Russek |
| 5,534,876 A | 7/1996 | Erikson et al. |
| 5,537,459 A | 7/1996 | Price et al. |
| 5,541,585 A | 7/1996 | Duhame et al. |
| 5,542,138 A | 8/1996 | Williams et al. |
| 5,544,649 A | 8/1996 | David et al. |
| 5,544,661 A | 8/1996 | Davis et al. |
| 5,548,637 A | 8/1996 | Heller et al. |
| 5,561,412 A | 10/1996 | Novak et al. |
| 5,572,195 A | 11/1996 | Heller et al. |
| 5,576,952 A | 11/1996 | Stutman et al. |
| 5,579,001 A | 11/1996 | Dempsey et al. |
| 5,579,775 A | 12/1996 | Dempsey et al. |
| 5,588,009 A | 12/1996 | Will |
| 5,592,153 A | 1/1997 | Welling et al. |
| 5,594,786 A | 1/1997 | Chaco et al. |
| 5,616,899 A | 4/1997 | Recigno |
| 5,627,524 A | 5/1997 | Fredrickson et al. |
| 5,628,324 A | 5/1997 | Sarbach |
| 5,633,742 A | 5/1997 | Shipley |
| 5,644,778 A | 7/1997 | Burks et al. |
| 5,678,562 A | 10/1997 | Sellers |
| 5,687,717 A | 11/1997 | Halpern et al. |
| 5,689,229 A | 11/1997 | Chaco et al. |
| 5,699,038 A | 12/1997 | Ulrich et al. |
| 5,712,795 A | 1/1998 | Layman et al. |
| 5,713,856 A | 2/1998 | Eggers et al. |
| 5,715,548 A | 2/1998 | Weismiller et al. |
| 5,719,761 A | 2/1998 | Gatti et al. |
| 5,724,025 A | 3/1998 | Tavori |
| 5,737,688 A | 4/1998 | Sakai et al. |
| 5,738,102 A | 4/1998 | Lemelson |
| 5,742,233 A | 4/1998 | Hoffman et al. |
| 5,748,907 A | 5/1998 | Crane |
| 5,752,917 A | 5/1998 | Fuchs |
| 5,771,511 A | 6/1998 | Kummer et al. |
| 5,772,585 A | 6/1998 | Lavin et al. |
| 5,772,599 A | 6/1998 | Nevo et al. |
| 5,781,442 A | 7/1998 | Engleson et al. |
| 5,788,851 A | 8/1998 | Kenley et al. |
| 5,800,387 A | 9/1998 | Duffy et al. |
| 5,822,418 A | 10/1998 | Yacenda et al. |
| 5,822,544 A | 10/1998 | Chaco et al. |
| 5,825,283 A | 10/1998 | Camhi |
| 5,836,910 A | 11/1998 | Duffy et al. |
| 5,838,223 A | 11/1998 | Gallant et al. |
| 5,850,221 A | 12/1998 | Macrae et al. |
| 5,862,803 A | 1/1999 | Besson et al. |
| H1782 H | 2/1999 | Wicks et al. |
| 5,872,505 A | 2/1999 | Wicks et al. |
| 5,873,369 A | 2/1999 | Laniado et al. |
| 5,895,354 A | 4/1999 | Simmons |
| 5,903,211 A | 5/1999 | Flego et al. |

| | | | | | | |
|---|---|---|---|---|---|---|
| 5,903,889 | A | 5/1999 | de la Huerga et al. | 6,533,729 B1 | 3/2003 | Khair et al. |
| 5,907,291 | A | 5/1999 | Chen et al. | 6,540,686 B2 | 4/2003 | Heikkiläet et al. |
| 5,911,687 | A | 6/1999 | Sato et al. | 6,544,173 B2 | 4/2003 | West et al. |
| 5,919,141 | A | 7/1999 | Money et al. | 6,544,174 B2 | 4/2003 | West et al. |
| 5,930,759 | A | 7/1999 | Moore et al. | 6,551,252 B2 | 4/2003 | Sackner et al. |
| 5,941,846 | A | 8/1999 | Duffy et al. | 6,559,620 B2 | 5/2003 | Zhou et al. |
| 5,944,659 | A | 8/1999 | Flach et al. | 6,569,094 B2 | 5/2003 | Suzuki et al. |
| 5,957,838 | A | 9/1999 | Rantala | 6,575,902 B1 | 6/2003 | Burton |
| 5,957,854 | A | 9/1999 | Beeson et al. | 6,577,893 B1 | 6/2003 | Beeson et al. |
| 5,961,448 | A | 10/1999 | Swenson et al. | 6,579,231 B1 | 6/2003 | Phipps |
| 5,970,387 | A | 10/1999 | Yuan | 6,589,170 B1 | 7/2003 | Flach et al. |
| 5,973,613 | A | 10/1999 | Reis et al. | 6,593,528 B2 | 7/2003 | Franklin-Lees et al. |
| 5,990,866 | A | 11/1999 | Yollin | 6,594,511 B2 | 7/2003 | Stone et al. |
| 6,009,333 | A | 12/1999 | Chaco | 6,595,929 B2 | 7/2003 | Stivoric et al. |
| 6,012,035 | A | 1/2000 | Freeman, Jr. et al. | 6,602,191 B2 | 8/2003 | Quy |
| 6,014,346 | A | 1/2000 | Malone | 6,603,401 B1 | 8/2003 | Ueyama |
| 6,018,713 | A | 1/2000 | Coli et al. | 6,605,038 B1 | 8/2003 | Teller et al. |
| 6,038,469 | A | 3/2000 | Karlsson et al. | 6,611,705 B2 | 8/2003 | Hopman et al. |
| 6,044,283 | A | 3/2000 | Fein et al. | 6,612,984 B1 | 9/2003 | Kerr, II |
| 6,044,382 | A | 3/2000 | Martino | 6,616,606 B1 | 9/2003 | Petersen et al. |
| 6,047,203 | A | 4/2000 | Sackner et al. | 6,640,246 B1 | 10/2003 | Gary, Jr. et al. |
| 6,055,506 | A | 4/2000 | Frasca, Jr. | 6,659,947 B1 | 12/2003 | Carter et al. |
| 6,057,758 | A | 5/2000 | Dempsey et al. | 6,669,630 B1 | 12/2003 | Joliat et al. |
| 6,057,782 | A | 5/2000 | Koenig | 6,671,563 B1 | 12/2003 | Engelson et al. |
| 6,074,345 | A | 6/2000 | van Oostrom et al. | 6,694,180 B1 | 2/2004 | Boesen |
| 6,078,261 | A | 6/2000 | Davsko | 6,723,046 B2 | 4/2004 | Lichtenstein et al. |
| 6,080,106 | A | 6/2000 | Lloyd et al. | 6,731,989 B2 | 5/2004 | Engleson et al. |
| 6,085,069 | A | 7/2000 | Sharpe | 6,736,759 B1 | 5/2004 | Stubbs et al. |
| 6,088,677 | A | 7/2000 | Spurgeon | 6,740,033 B1 | 5/2004 | Olejniczak et al. |
| 6,093,146 | A | 7/2000 | Filangeri | 6,748,250 B1 | 6/2004 | Berman et al. |
| 6,125,350 | A | 9/2000 | Dirbas | 6,749,566 B2 | 6/2004 | Russ |
| 6,132,371 | A | 10/2000 | Dempsey et al. | 6,758,812 B2 | 7/2004 | Lang |
| 6,135,949 | A | 10/2000 | Russo et al. | 6,773,396 B2 | 8/2004 | Flach et al. |
| 6,141,531 | A | 10/2000 | Williams et al. | 6,779,024 B2 | 8/2004 | DeLaHuerga |
| 6,144,848 | A | 11/2000 | Walsh et al. | 6,819,247 B2 | 11/2004 | Birnbach et al. |
| 6,147,592 | A | 11/2000 | Ulrich et al. | 7,092,376 B2 | 8/2006 | Schuman |
| 6,147,618 | A | 11/2000 | Halleck et al. | 7,315,535 B2 | 1/2008 | Schuman |
| 6,150,951 | A | 11/2000 | Olejniczak | 7,715,387 B2 | 5/2010 | Schuman |
| 6,159,147 | A | 12/2000 | Lichter et al. | 2001/0034475 A1 | 10/2001 | Flach et al. |
| 6,160,478 | A | 12/2000 | Jacobsen et al. | 2002/0158919 A1 | 10/2002 | Nacey |
| 6,167,258 | A | 12/2000 | Schmidt et al. | 2002/0165731 A1 | 11/2002 | Dempsey |
| 6,171,264 | B1 | 1/2001 | Bader | 2002/0198986 A1 | 12/2002 | Dempsey |
| 6,186,962 | B1 | 2/2001 | Lloyd et al. | 2003/0078810 A1 | 4/2003 | Cole et al. |
| 6,198,394 | B1 | 3/2001 | Jacobsen et al. | 2003/0078811 A1 | 4/2003 | Cole et al. |
| 6,213,942 | B1 | 4/2001 | Flach et al. | 2004/0128168 A1 | 7/2004 | Wyatt |
| 6,230,142 | B1 | 5/2001 | Benigno et al. | 2004/0243446 A1 | 12/2004 | Wyatt |
| 6,259,355 | B1 | 7/2001 | Chaco et al. | 2005/0219059 A1 | 10/2005 | Ulrich et al. |
| 6,270,457 | B1 | 8/2001 | Bardy | 2006/0114888 A1 | 6/2006 | Schuman |
| 6,277,080 | B1 | 8/2001 | Nissilä et al. | 2008/0095156 A1 | 4/2008 | Schuman |
| 6,279,183 | B1 | 8/2001 | Kummer et al. | | | |
| 6,289,238 | B1 | 9/2001 | Beeson et al. | | FOREIGN PATENT DOCUMENTS | |
| 6,304,774 | B1 | 10/2001 | Gorman | | | |
| 6,336,900 | B1 | 1/2002 | Alleckson et al. | DE | 37 35 295 | 4/1988 |
| 6,336,903 | B1 | 1/2002 | Bardy | EP | 0 468 366 | 1/1992 |
| 6,344,794 | B1 | 2/2002 | Ulrich et al. | EP | 0 505 627 | 9/1992 |
| 6,356,874 | B1 | 3/2002 | Ohrn | EP | 0 578 374 | 1/1994 |
| 6,368,284 | B1 | 4/2002 | Bardy | EP | 0 780 111 | 6/1997 |
| 6,398,727 | B1 | 6/2002 | Bui et al. | EP | 0 872 998 | 10/1998 |
| 6,398,728 | B1 | 6/2002 | Bardy | EP | 0 748 566 | 5/1999 |
| 6,402,691 | B1 | 6/2002 | Peddicord et al. | EP | 1 017 032 A2 | 7/2000 |
| 6,406,426 | B1 | 6/2002 | Reuss et al. | EP | 1 018 715 A1 | 7/2000 |
| 6,407,335 | B1 | 6/2002 | Franklin-Lees et al. | EP | 1 020 827 A1 | 7/2000 |
| 6,411,840 | B1 | 6/2002 | Bardy | EP | 1 033 901 A2 | 9/2000 |
| 6,416,471 | B1 | 7/2002 | Kumar et al. | ES | 2 077 512 | 11/1995 |
| 6,441,747 | B1 | 8/2002 | Khair et al. | GB | 2 190 535 A | 11/1987 |
| 6,443,890 | B1 | 9/2002 | Schulze et al. | GB | 2 193 359 A | 2/1988 |
| 6,450,953 | B1 | 9/2002 | Place et al. | GB | 2 230 365 A | 10/1990 |
| 6,475,153 | B1 | 11/2002 | Khair et al. | GB | 2 265 038 A | 9/1993 |
| 6,493,747 | B2 | 12/2002 | Simmon et al. | JP | 4061858 | 2/1992 |
| 6,494,829 | B1 | 12/2002 | New, Jr. et al. | JP | 5268373 | 10/1993 |
| 6,496,705 | B1 | 12/2002 | Ng et al. | JP | 7074835 | 3/1995 |
| 6,497,656 | B1 | 12/2002 | Evans et al. | JP | 8131407 | 5/1996 |
| 6,517,497 | B2 | 2/2003 | Rymut et al. | JP | 8150182 | 6/1996 |

| | | |
|---|---|---|
| JP | 8154901 | 6/1996 |
| JP | 8173487 | 7/1996 |
| JP | 8287383 | 11/1996 |
| JP | 9038050 | 2/1997 |
| JP | 9044572 | 2/1997 |
| JP | 9130490 | 5/1997 |
| WO | WO 91/05311 | 4/1991 |
| WO | WO 92/09178 | 5/1992 |
| WO | WO 94/13198 | 6/1994 |
| WO | WO 94/22098 | 9/1994 |
| WO | WO 94/27544 | 12/1994 |
| WO | WO 95/03596 | 2/1995 |
| WO | WO 95/15064 | 6/1995 |
| WO | WO 95/23378 | 8/1995 |
| WO | WO 95/23478 | 8/1995 |
| WO | WO 95/35634 | 12/1995 |
| WO | WO 96/25738 | 8/1996 |
| WO | WO 97/15240 | 5/1997 |
| WO | WO 97/40640 | 10/1997 |
| WO | WO 99/12329 | 3/1999 |
| WO | WO 99/13766 | 3/1999 |
| WO | WO 99/23623 | 5/1999 |
| WO | WO 99/24899 | 5/1999 |
| WO | WO 99/52487 | 10/1999 |
| WO | WO 00/59166 | 10/2000 |

OTHER PUBLICATIONS

Fred Theil, "Convergence in the Post-PC Era", Health Management Technology, Feb. 2000.

Futura & Futura II, Executone Information Systems, Inc.

Bob Livermore, "Health Service Applications in England and Wales".

IBM Technical Disclosure Bulletin, Portable, Speech-Activated, Electronic Mail System, vol. 38, No. 7, Jul. 1995.

INFOSTAR/ILS . . . TM . . . Integrated Locating System, 1999 Executone Information Systems, Inc.

Infra-Com.RTM. A Staff and Equipment Locating and Signaling System from United Identification Systems Corp., 1993.

Infrared Locator, Teleconnect, Feb. 1986.

Keeping Track of Alzheimer and Dementia Prone Patients Just Got Easier, WanderCare System 1991.

Ooi, et al., "Low Cost RF Identification and Locating System", Apr. 12, 1989.

Responder.RTM. III Plus, Health Care Communication System, Quality Care . . . A Touch Away, Rauland.

Sekurmed, Infant Monitoring System.

Weiser, Mark, "The Computer for the 21.Sup.St Century", Scientific American, Sep. 1991.

The Intelligent Partner, 1992 Executone Information Systems, Inc.

The LifeSaver.TM. Nurse Call System, Executone Brochure.

Artusi, Daniel, "The Technology of Smartcards and Their Applications".

Written Opinion for PCT/US98/22908, dated Dec. 2, 1999, (4 pages).

ComLinx Enterprise Solutions—Nurse Communication Module—User's guide, Hill-Rom Services, Inc., (2000).

HEALTHCARE COMPUTER SYSTEM

This application is a continuation of U.S. patent application Ser. No. 11/959,660 which was filed Dec. 19, 2007, issued as U.S. Pat. No. 7,715,387, which is a continuation of U.S. patent application Ser. No. 11/330,021 which was filed Jan. 11, 2006, issued as U.S. Pat. No. 7,315,535, which is a continuation of U.S. patent application Ser. No. 10/114,682 which was filed Apr. 1, 2002, issued as U.S. Pat. No. 7,092,376, and which claimed the benefit of U.S. Provisional Application No. 60/280,002 which was filed Mar. 30, 2001; each of which are hereby incorporated by reference herein.

BACKGROUND AND SUMMARY OF THE INVENTION

The present invention relates to a hospital bed and network communication system. More particularly, the present invention relates to a bed in a patient/nurse call system in a hospital network with voice communication implemented over message packets via a packet based communication network.

Almost every hospital wing or ward has a patient/nurse call system that includes an audio network to allow a patient in a hospital room to contact and speak with a nurse or staff member at a nurse station. Typically, the patient may activate a "call" signal by depressing a button on a small housing connected via hardwire to a unit mounted to the headwall of the patient room. This small housing is generally referred to as a pillow speaker, or pillow unit. The headwall unit usually has another wall-mounted call button for easy operation by a nurse. Other input mechanisms may include emergency call buttons, code blue buttons, or bathroom call buttons. Additionally, the audio network of these call systems may be used for audio monitoring of a hospital room from the nurse station during an extreme emergency, such as a code "blue" status.

Hospitals also include emergency signaling devices for notifying hospital personnel of other types of emergency conditions, such as smoke detectors or a fire alarm. Typically, these devices generate audio signals to convey audible alarms over a hospital intercom system, which may or may not be interconnected with the patient room audio network. Some hospitals also use bed monitoring devices with bed sensors that indicate bed conditions such as "brakes on," mattress firmness (for inflatable mattresses), or incontinence.

Historically, the duplicity of call and information systems in hospitals has complicated the organization, maintenance and effective dissemination of all of the useful information that is generated. If these systems cannot be operated in a simple, user-friendly manner, they can add to the stress level of nurses and staff. As a result, their jobs are made more difficult, rather than made easier. Additionally, use of multiple call and information systems in a hospital adds to the costs of health care, due to costs associated with purchase, installation and maintenance of the various components of these multiple systems, along with training personnel how to use the system.

U.S. Pat. Nos. 5,561,412, 5,699,038, and 5,838,223, which are incorporated herein by reference, disclose integration of call and information systems through a private branch exchange ("PBX") voice/data switching system that establishes audio links and data distribution between a master station and other stations. The disclosed communications networks are basically telephone networks that provide synchronous, full duplex, voice and data communications. Additionally, non-voice information signals from emergency signaling devices, bed monitoring devices, locating and tracking transmitters, and/or various other pieces of equipment are converted to digital data and transmitted through the PBX to the distant end over a low-speed channel.

Although PBX based systems provide several advantages over historical approaches, there are still needs to reduce equipment and maintenance costs, to increase expandability and versatility, and to increase the effective bandwidth of patient/nurse call systems in hospital networks.

The present invention fulfills the above needs, among others, by providing a system and method for a hospital bed, a patient/nurse call, and a hospital network using voice and data over packet implementation.

In one illustrated embodiment of the present invention, a patient/nurse call system comprises a plurality of transmitters adapted to be carried by hospital personnel, each transmitter being configured to periodically transmit an identification signal unique to that transmitter, a plurality of patient locations, each of the plurality of patient locations being associated with a patient and including a receiver configured to receive the identification signals from the plurality of transmitters, and a master station remote from the patient locations, the master station being configured to receive signals from the receivers to indicate locations of the hospital personnel. The system also comprises a packet based communication network, and a plurality of first audio stations coupled to the packet based communication network. A first audio station is located at each patient location and is identified by a unique address. Each first audio station includes a first processor, a first microphone, a first speaker, and a first converter configured to receive audio signals from the first microphone, to generate voice data in a packet based data stream corresponding thereto, and to transmit the packet based data stream over the communication network. The first converter also is configured to receive a packet based data stream from the communication network, to generate audio signals corresponding thereto, and to transmit the audio signals to the first speaker. The system further comprises a second audio station located at the master station and coupled to the packet based communication network. The second audio station is identified by a unique address and includes a second processor, a second microphone, a second speaker, and a second converter configured to receive audio signals from the second microphone, to generate voice data in a packet based data stream corresponding thereto, and to transmit the packet based data stream over the communication network. The second converter also is configured to receive a packet based data stream from the communication network, to generate audio signals corresponding thereto, and to transmit the audio signals to the second speaker, thereby permitting audio communication between personnel located at the first and second audio stations.

In an illustrated embodiment, a server is coupled to the packet based communication network. The server is configured to instruct the plurality of first audio stations to send the packet based data stream to and receive the packet based data stream from the second audio station. The server is further configured to instruct the second audio station to send the packet based data stream to and receive the packet based data stream from the first audio stations.

In another illustrated embodiment of the present invention, a patient/nurse call system comprises a packet based communication network, a plurality of transmitters, each of the transmitters being configured to be carried by a hospital caregiver and to periodically transmit an identification signal that identifies the transmitters and a plurality of receivers configured to receive the identification signals and generate identification data corresponding thereto. The receivers are configured to convert the identification data into a packet based data stream and to transmit the packet based data stream over the communication network. The system also includes a first audio station coupled to the packet based communication network and being identified by a unique address. The first audio station includes a first processor, a first microphone, a first speaker, and a first converter configured to receive audio signals from the first microphone, to generate voice data in a packet based data stream corresponding thereto, and to transmit the packet based data stream over the communication network. The first converter also is configured to receive a packet based data stream from the communication network, to generate audio signals corresponding thereto, and to transmit the audio signals to the first speaker. The system further includes a second audio station coupled to the packet based communication network and being identified by a unique address. The second audio station includes a second processor, a second microphone, a second speaker, and a second converter configured to receive audio signals from the second microphone, to generate voice data in a packet based data stream corresponding thereto, and to transmit the packet based data stream over the communication network. The second converter also is configured to receive a packet based data stream from the communication network, to generate audio signals corresponding thereto, and to transmit the audio signals to the second speaker. The system still further includes a server coupled to the receivers, the first audio station, and the second audio station via the packet based communication network. The server is configured to instruct the first audio station and the second audio station regarding at least one of establishing an audio connection and terminating an audio connection based at least in part on the identification data, thereby permitting audio communication between personnel located at the first and second audio stations.

In the illustrated embodiment, the receiver is further configured to generate location data based at least in part on the identification signals, and the server is further configured to instruct the first audio station and the second audio station regarding at least one of establishing an audio connection and terminating an audio connection based at least in part on the location data.

In yet another illustrated embodiment of the present invention, a method for patient and nurse communication over a hospital network comprises the steps of receiving at least one of an identification signal from a transmitter carried by a hospital caregiver, a bed status signal, a chair call signal, a shower status signal, and a remote code signal, generating non-voice data corresponding to the received signal, and generating voice data. The method also includes sending a first notification packet from a first address into a packet network, sending a first request packet from a second address into the packet network in response to the first notification packet, transporting the non-voice data in packets between the first address and the second address in response to the first notification packet and the first request packet, and transporting the voice data in packets between the first address and the second address in response to the first notification packet and the first request packet.

In a further illustrated embodiment of the present invention, a patient support apparatus comprises a patient support, and a computer coupled to the patient support. The computer provides an audio station on the patient support configured to communicate with a packet based communication network. A display coupled to the computer. A data device is also coupled to the computer. The data device includes at least one of a psychological monitor, a treatment device, and a therapy device, the computer being configured to receive data from the data device, convert the data received from the data device to a packet based data stream, and transmit the packet based data stream to the packet based communication network.

In an illustrated embodiment, a plurality of data devices are coupled to the computer including an input device to input data and instructions concerning the patient, and a sensing device including at least one of a heart rate sensor, a respiratory rate sensor, a neurological monitoring sensor, and a temperature sensor. Also in illustrated embodiments, the data device includes at least one of a vital signs monitor, an IV pump, a ventilator, a defibrillator, and a compression boot. In illustrated embodiments, the patient support is a hospital bed or a patient assist cart.

Additional features of the invention will become apparent to those skilled in the art upon consideration of the following detailed description of the drawings exemplifying the best mode of carrying out the invention as presently perceived.

DETAILED DESCRIPTION OF THE DRAWINGS

Transmitting voice data and/or non-voice data in packets over a network requires that a protocol be selected and implemented. Protocols specify methods for encoding, packetizing, and decoding voice signals as well as for call signaling, controlling, and packet exchange. Several competing protocols have been developed. The leading protocol to date is H.323 developed by the International Telecommunications Union. (ITU). Another protocol is Session Initiation Protocol (SIP) developed by the Internet Engineering Task Force (IETF). Media Gateway Control Protocol (MGCP) and Megaco are two others. Most protocols are suitable for transmission of voice over an Internet Protocol (IP) network. However, some protocols will also support voice over an Asynchronous Transfer Mode (ATM) network. In any event, one of ordinary skill in the art will readily appreciate that a number of well known protocols may be used in alternative embodiments of the present invention.

Figure 1:
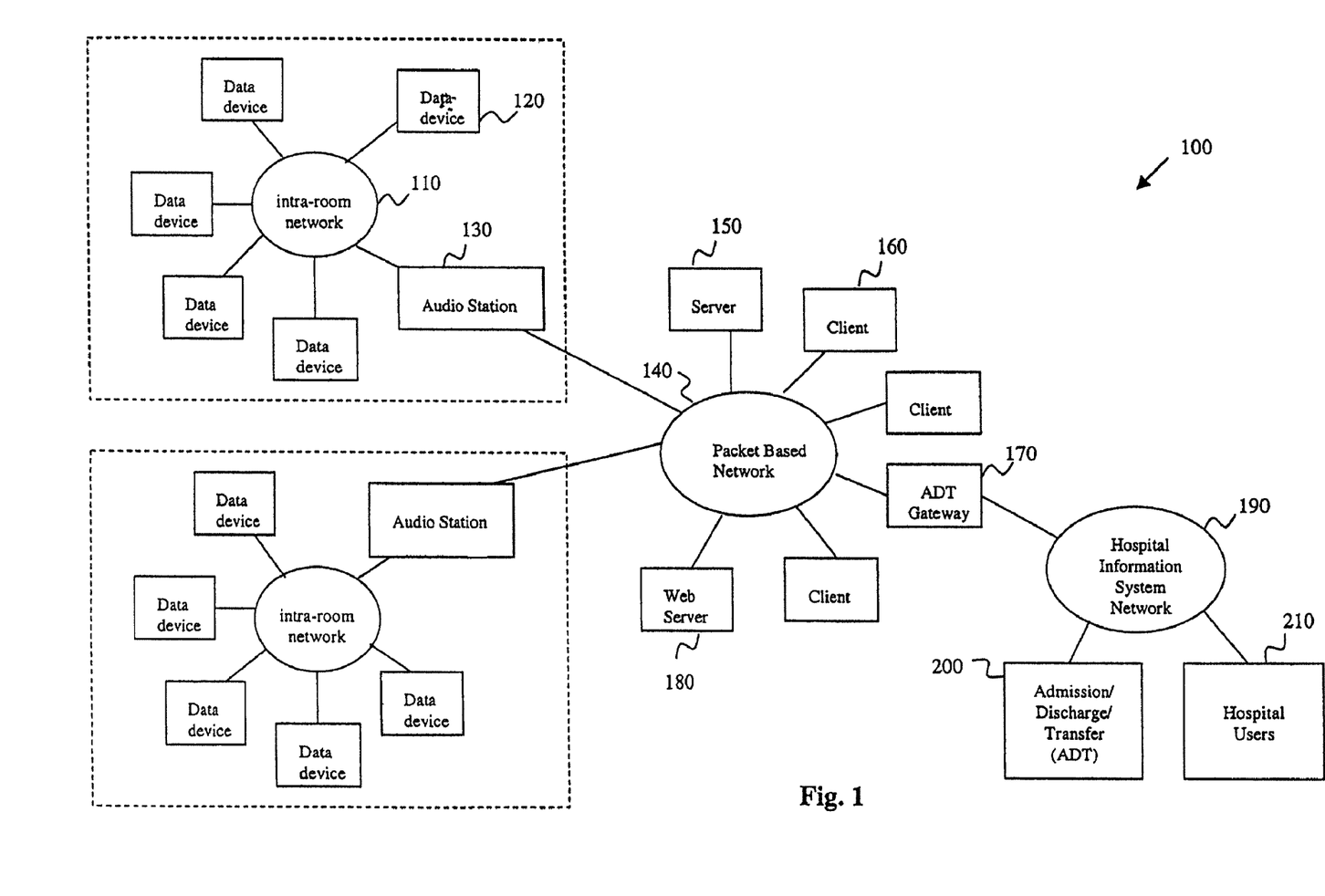
FIG. 1 is an illustrative architecture of a system for transmitting voice and data in packets over a network.

FIG. 1 is an illustrative architecture of a system 100 for transmitting voice and data in packets over a network. The system 100 includes any suitable number of intra-room networks 110. Each intra-room network 110 couples a number of data devices 120 to an audio station 130 (discussed in further detail below). For example, U.S. Pat. Nos. 5,561,412; 5,699,038; and 5,838,223 (which have been incorporated herein by reference) disclose similar intra-room networks. Each data device 120 is suitably configured to receive inputs from various hospital beds, patient/nurse call systems, and/or personnel and asset locating and tracking systems and to communicate the corresponding information to the respective audio station 130.

Each audio station 130 (discussed in further detail below) couples the respective intra-room network 110 to a packet based network 140. In the exemplary embodiment, the packet based network is configured in a "client/server" (or "two-tier") architecture. In a typical client/server architecture, each computer or process of a system is viewed as either a "client" or a "server." Generally, a server manages network resources such as file storage, printing operations, database queries, network communications, etc. To enhance efficiency, various servers may be dedicated to the management of various different resources. For example, a computer that provides (i.e., "serves up") Internet access is sometimes referred to as a "web server." A client generally provides a user interface and often provides additional processing power remote from the server. Typically, clients can share files and programs amongst themselves as well as retrieve data from the server(s). In any event, the packet based network 140 may be any suitable collection of devices that is connected to share information in packets. To this end, it should be readily appreciated that the packet based network 140 may include multiple Local Area Networks ("LANs") and/or Wide Area Networks ("WANs") that are operably coupled to one another via routers, switches, hubs, gateways, proxies, and/or firewalls (not shown). However, although the exemplary network 140 is implemented in a client/server architecture, it is noted that alternative embodiments may be implemented in a peer-to-peer architecture or any other suitable configuration.

In general, in the exemplary client/server architecture (noted above) each audio station 130 is configured to operate as a client on the packet based network 140. Accordingly, each exemplary audio station 130 is illustratively implemented with a personal computer system, a desktop computer system, and/or a workstation manufactured by Dell Computer Corporation of Round Rock, Tex., Gateway, Inc. of San Diego, Calif., or Compaq Computer Corporation of Houston, Tex. It should be appreciated that each audio station 130 may alternatively, or in addition, include a network appliance and/or any other suitable packet based network enabled device.

Additionally, each audio station 130 includes a microphone (not shown) that provides an analog signal to a code-decode ("CODEC") integrated circuit ("IC") (not shown). The CODEC periodically samples the analog voice signal and generates numerical values representing the amplitudes of the signal at the sample times. The sampling is done a rate high enough to ensure the voice can be recreated with good quality by equipment located at a remote or distant end of the system, such as, for example, another of the audio stations 130 or a server computer 150 that is coupled to the packet based network 140. Each audio station 130 further includes a speaker (not shown) and a digital-to-analog ("D/A") converter (not shown). The D/A receives numerical values representing audio signals and generates corresponding analog signals, which drive the speaker.

Each audio station has an address that identifies it on the packet based network 140. To transmit data, an audio station 130 builds digital signals into a message packet along with all the header information such as source address, destination address, checksum, packet size, etc. Each message is transmitted onto the network and is addressed to another audio station at the distant end. For voice data, the distant end station converts the digital signal to analog for sounding through its speaker. To ensure good voice quality, packets are consistently delivered to the distant end at a rate as fast as they are sampled at the originating audio station 130. It should be readily appreciated that any suitable number of similarly configured audio stations 130 and/or other devices may be coupled to the packet based network 140 to effectuate the communication of voice and other information as discussed in further detail below.

The server computer 150 is configured to provide server operations for the packet based network 140. To this end, the exemplary server computer 140 is illustratively implemented with a server computer system manufactured by Dell Computer Corporation of Round Rock, Tex., Gateway, Inc. of San Diego, Calif., or Compaq Computer Corporation of Houston, Tex. Further, the server computing device 140 may alternatively, or in addition, include network server appliances, server farms, server clusters, network accessible storage devices, and/or any other device suitable for executing operations according to the present invention. The server computer 150 is further configured to code and decode voice signals and data in a similar manner to the audio station 130.

It should be readily appreciated that any suitable number of packet based devices (such as, for example, client computer 160, Admission/Discharge/Transfer system ("ADT") gateway 170, and/or web server 180, etc.) may be coupled to the packet based network 140 to effectuate packet based communication of any suitable information into or out of the packet based network 140 in a manner which is well known. Furthermore, it should be appreciated that such additional packet based devices may in turn be suitably coupled to other networks (such as, for example, hospital information system network 190, etc.), which may in turn be suitably coupled to their own respective databases (such as, for example, ADT database 200, etc.) and/or their respective user interfaces (such as, for example, ADT hospital users 210, etc.).

Figure 2:
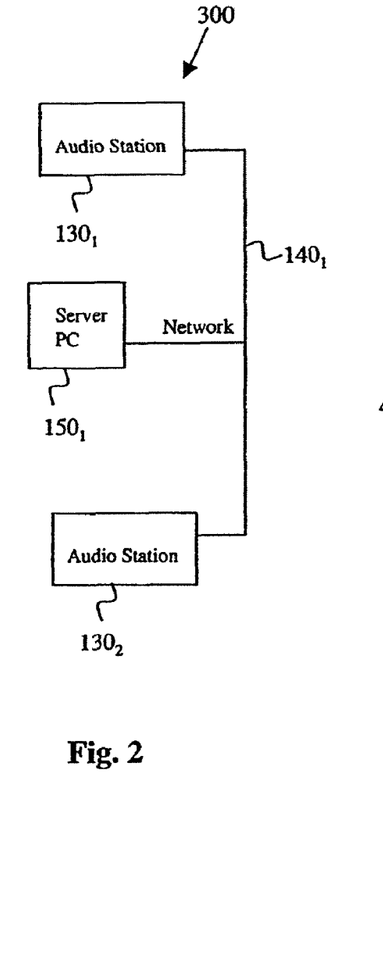
FIG. 2 is an illustrative system architecture interconnecting two audio stations and a server computer.
Figure 3:
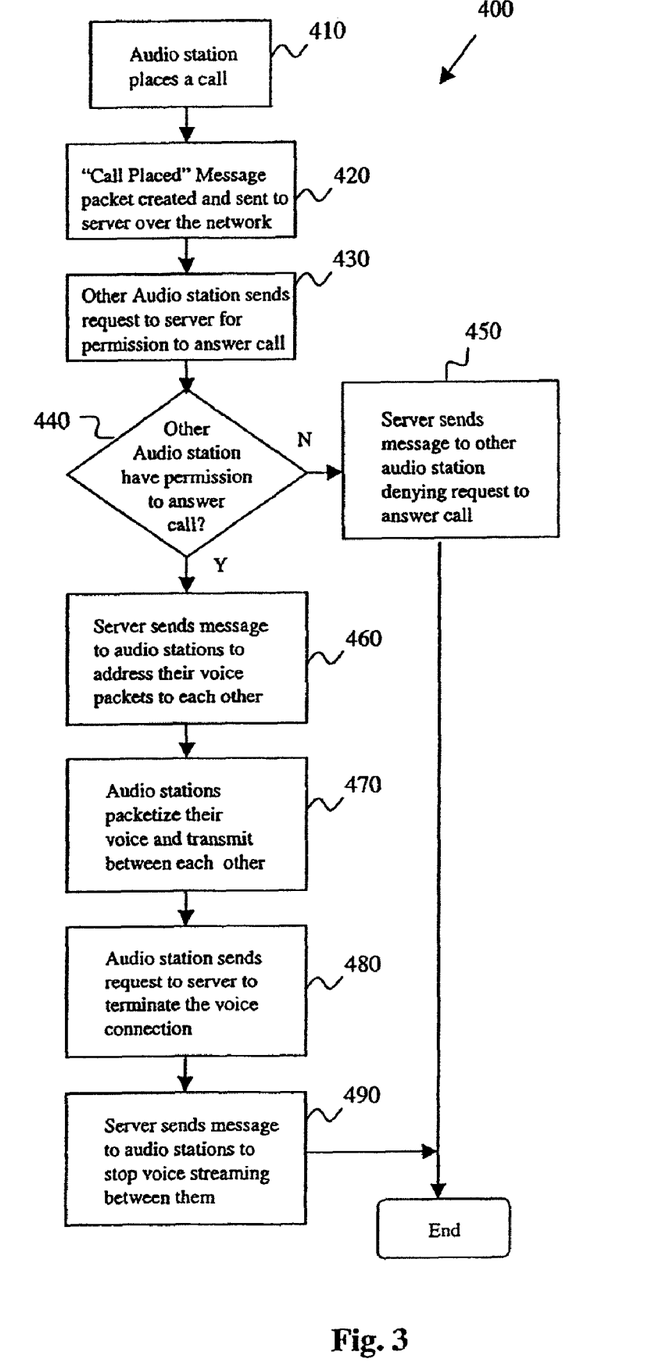
FIG. 3 is an illustrative flow diagram for a process of voice over packet communication between the two audio stations in the system illustrated in FIG. 2.

FIG. 2 is an illustrative system architecture 300 interconnecting two audio stations $130_1$, $130_2$ and a server computer $150_1$ with a packet based network $140_1$. Exemplary audio station $130_1$, exemplary audio station $130_2$, exemplary server computer $150_1$, and exemplary packet based network $140_1$ are implemented in similar manners to audio station(s) 130, server computer 150, and packet based network 140, respectively (discussed above in connection with FIG. 1). FIG. 3 is an illustrative flow diagram for a process 400 of voice over packet communication between the two audio stations $130_1$, $130_2$ in the system illustrated in FIG. 2.

At step 410, audio station $130_1$ initiates a call. It should be appreciated that the call may be in response to a user input (for example, actuation of a call button by a caregiver or a patient) or an automatic signal from monitoring equipment that is provided to audio station $130_1$ by a data device (see FIG. 1).

Upon initiation of the call, audio station $130_1$ sends a message over network $140_1$ to server computer $150_1$ (step 420). Server computer $150_1$ displays this call information on a user terminal and also searches a database to determine which patient room the call is from and what caregiver is assigned to that patient. If a caregiver at audio station 1302 wants to answer the call, then that caregiver inputs a request into audio station $130_2$ to answer the call through a suitable user interface and/or data device. In response to the request to answer the call, at step 430 audio station $130_2$ sends a request to server computer $150_1$ for permission to establish an audio connection with station audio station $130_1$.

At step 440, server computer $150_1$ determines whether the caregiver at audio station $130_2$ should have permission to take the call. It should be appreciated that server computer $150_1$ may make this determination based on predetermined software logic which may consider inputs from other system users (such as, for example, a head or "charge" nurse who is provided an indication of the call request status by server computer $150_1$ or any other manager or supervisor), which may alternatively or in addition consider location and/or tracking information from a data device(s) that indicates the identity and whereabouts of the caregiver who is requesting to answer the call (see FIG. 10), and/or which may consider any other suitable inputs or variables.

If the server computer $150_1$ determines at step 440 that permission not granted for the caregiver at audio station $130_2$ to answer the call, then at step 450 server computer $150_1$ sends a message to audio station $130_2$ indicating a denial of the request to answer the call and the server computer $150_1$ terminates the process 400.

If the server computer $150_1$ determines at step 440 that permission granted for the caregiver at audio station $130_2$ to answer the call, then server computer $150_1$ bypasses step 450 and at step 460 the server computer $150_1$ sends a message(s) over network $140_1$ to audio stations $130_1$, $130_2$ that instructs them to transmit their voice packets to each other over the network $140_1$, thereby establishing a voice connection. At step 470, audio stations $130_1$, $130_2$ build their voice data into message packets (i.e., they "packetize" the voice data) in response to the instruction(s) from server computer $150_1$ to transmit voice packets, and they transmit the packets between each other.

At step 480, the caregiver at audio stations $130_2$ initiates a request to end the audio connection (or to "hang up"). It is noted that the request to end the call may include an active request (such as, for example, actuation of a "voice end" button), and in alternative embodiments may in addition or alternatively include a passive request (such as, for example, a locating and tracking detection that the caregiver has left a proximity of the audio stations $130_2$). In response to the request to end the audio connection, audio station $130_2$ sends a message to server computer $140_1$ that requests termination of the audio connection. In response to the request to termination the audio connection generated at step 480, at step 490 server computer $150_1$ sends a message to both audio stations $130_1$, $130_2$ that instructs them to stop their voice transmissions, thereby terminating the audio connection.

Figure 4:
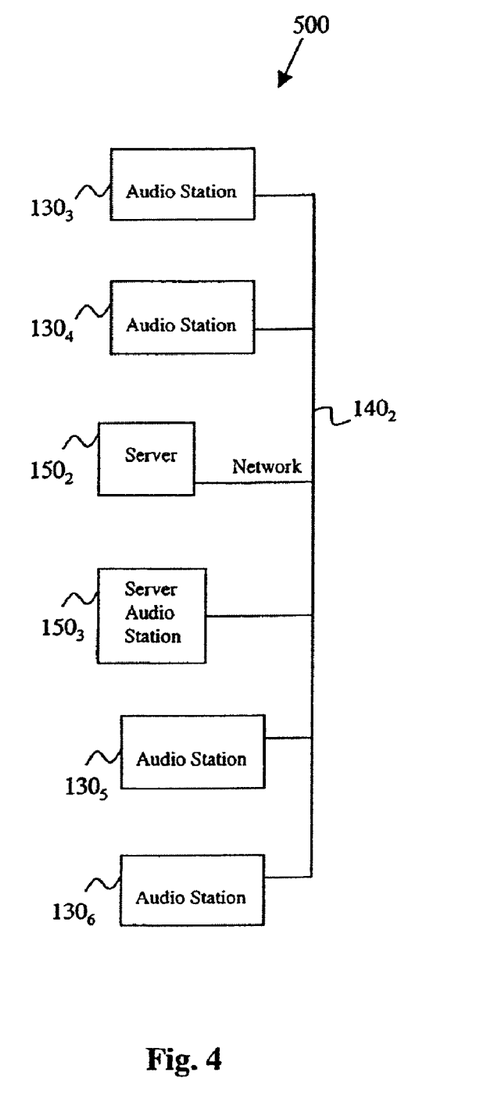
FIG. 4 is an illustrative system architecture interconnecting multiple audio stations, a server computer, and a server audio station.

Next, FIG. 4 is an illustrative system architecture 500 interconnecting multiple audio stations $130_3$, $130_4$, $130_5$, $130_6$, a server computer $150_2$, and a server audio station $150_3$. This exemplary embodiment provides a paging feature. Paging consists of transmitting voice from one audio station to one or more additional audio stations in one direction only. It should be appreciated that exemplary audio stations $130_3$, $130_4$, $130_5$, $130_6$, exemplary server computer $150_2$, and exemplary packet based network $140_2$ are implemented in similar manners to audio station(s) 130, server computer 150, and packet based network 140, respectively (discussed above in connection with FIG. 1); and exemplary server audio station $150_3$ is implemented in a similar manner to server computer 150 (with suitable software and/or hardware modifications to perform the relevant operations discussed herein).

Figure 5:
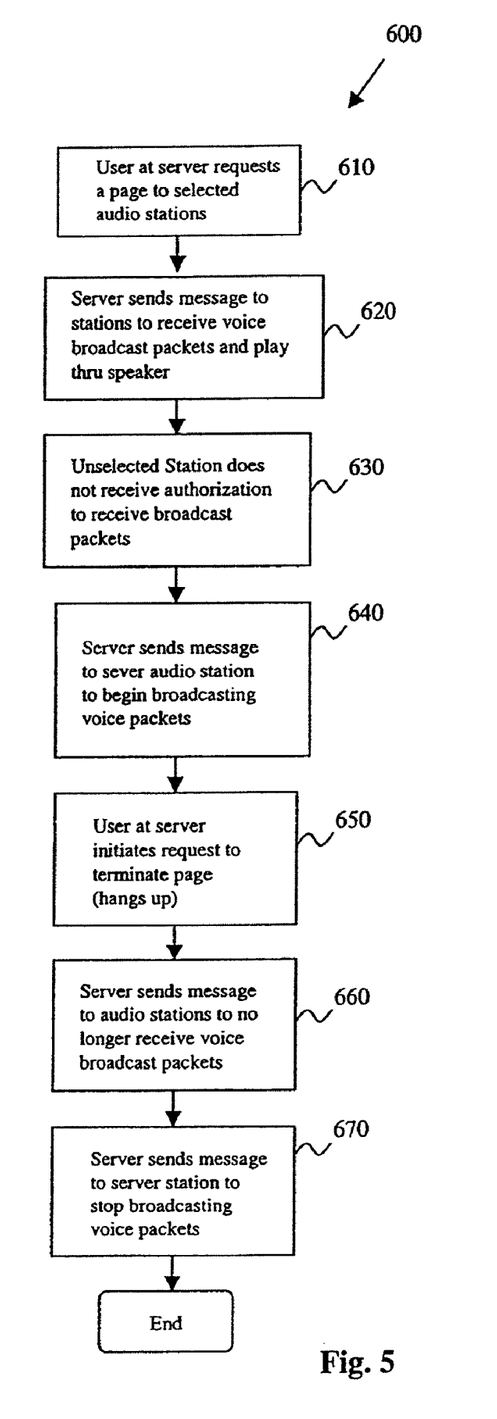
FIG. 5 is an illustrative flow diagram of a first process of voice over packet paging for the system illustrated in FIG. 4.

FIG. 5 is an illustrative flow diagram of a first process 600 of voice over packet paging for the system illustrated in FIG. 4. To send a page, at step 610 a user inputs a request to server computer $150_2$ to initiate a selected page to desired audio stations. The discussion that follows in connection with FIG. 5 assumes (as an example) that audio stations $130_3$, $130_4$, $130_5$ are selected. At step 620, server computer $150_2$ sends instructions to the selected audio stations (the "page group") to receive voice broadcast (page) packets and generate corresponding sounds via their speakers. It is noted that any audio stations not selected do not receive such instructions (see step 630).

At step 640, server computer $150_2$ sends instructions to server audio station $150_3$ to begin broadcasting the selected page in voice data packets. The page is broadcast suitably repeatedly until the user terminates the page (see step 650).

At step 650, the user inputs a request to terminate the page (or to "hang up") into server computer $150_2$. The request to end the page may include an active request (such as, for example, actuation of a "page end" button), and in alternative embodiments may in addition or alternatively include a passive request (such as, for example, a locating and tracking detection that the user has left a proximity of the server computer $150_2$).

At step 660, the server computer $150_2$ sends instructions to the previously selected audio stations (see step 620, above) to stop sounding voice broadcast (page) packets. At step 670, server computer $150_2$ sends instructions to server audio station $150_3$ to stop broadcasting the voice packets.

Figure 6:
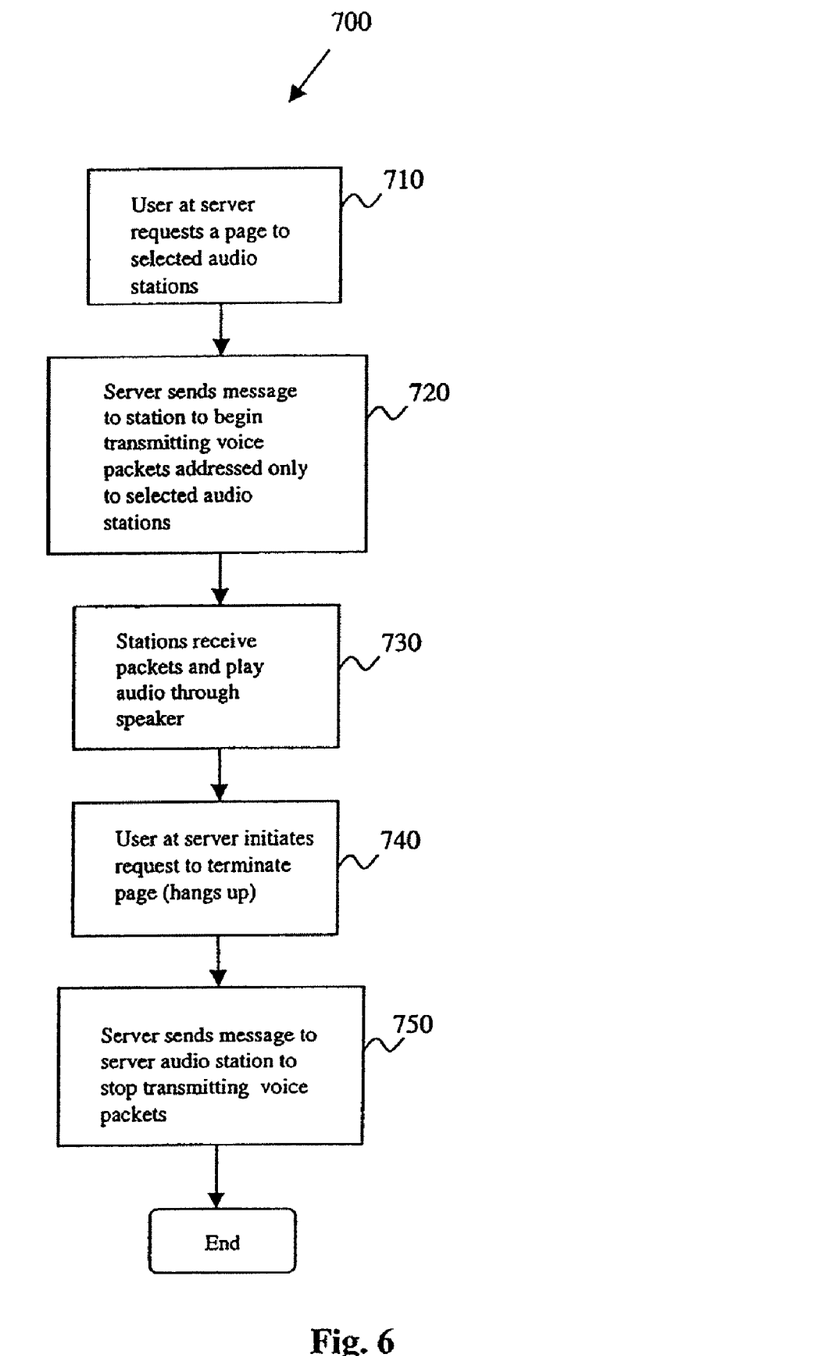
FIG. 6 is an illustrative flow diagram of a second process of voice over packet paging for the system illustrated in FIG. 4.

FIG. 6 is an illustrative flow diagram of a second process 700 of voice over packet paging for the system illustrated in FIG. 4. To send a page using the process 700, at step 710 a user inputs a request to server computer $150_2$ to initiate a selected page to desired audio stations. The discussion that follows in connection with FIG. 6 assumes (as an example) that audio stations $130_3$, $130_4$, $130_5$ are selected. At step 720, server computer $150_2$ sends instructions to server audio station $150_3$ to transmit the selected page in voice data packets addressed specifically (and only) to the selected audio stations $150_2$. At step 730, the selected audio stations receive the page packets and produce corresponding audio from their speakers.

At step 740, the user inputs a request to terminate the page (or to "hang up") into server computer $150_2$. The request to end the page may include an active request (such as, for example, actuation of a "page end" button), and in alternative embodiments may in addition or alternatively include a passive request (such as, for example, a locating and tracking detection that the user has left a proximity of the server computer $150_2$). At step 750, server computer $150_2$ sends instructions to server audio station $150_3$ to stop broadcasting the voice packets.

Figure 7:
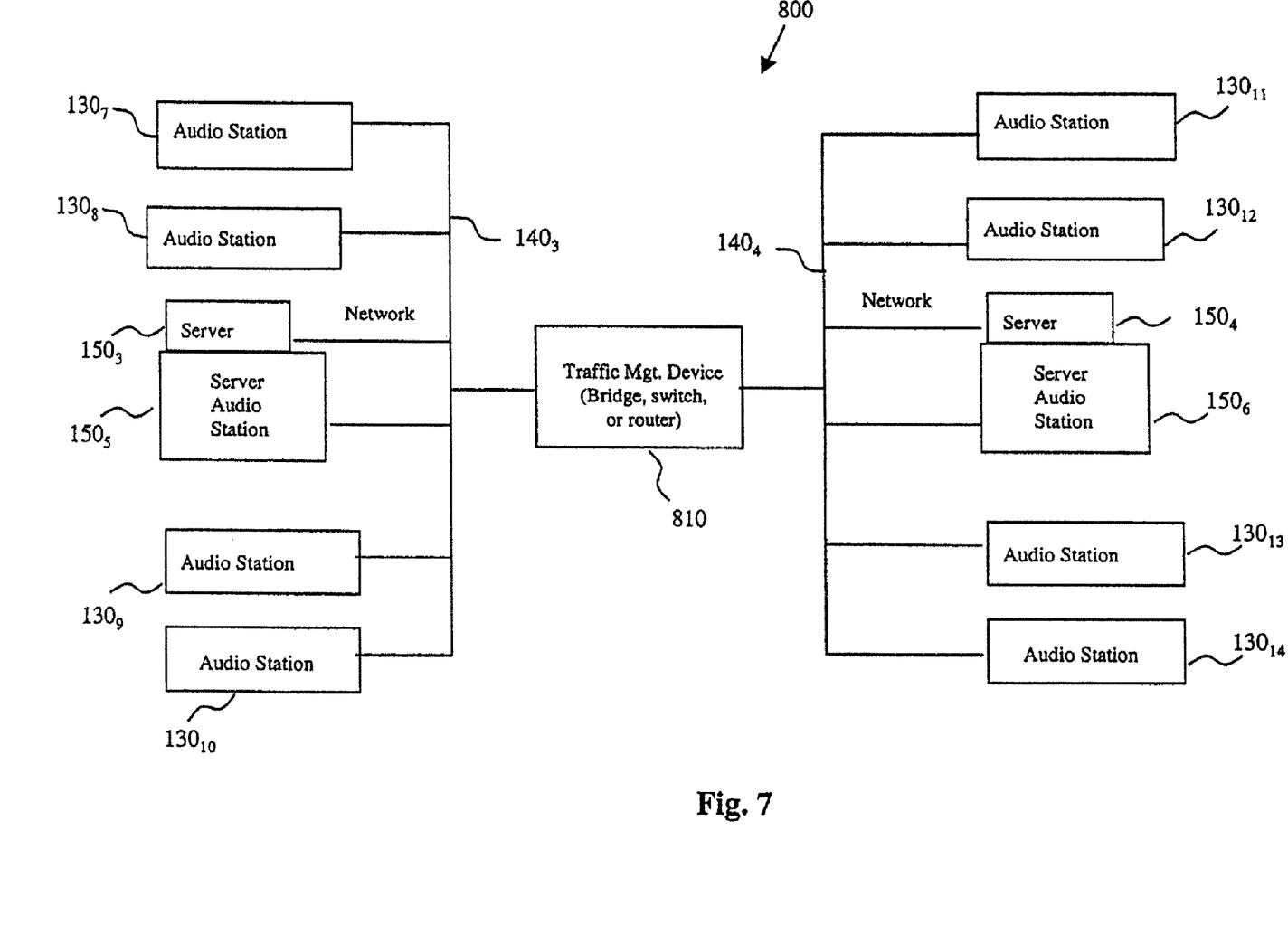
FIG. 7 is an illustrative system architecture that interconnects multiple audio stations, multiple server computers, and multiple server audio stations through a traffic management device.

FIG. 7 is an illustrative system architecture 800 that interconnects multiple audio stations $130_7$, $130_8$, $130_9$, $130_{10}$, $130_{11}$, $130_{12}$, $130_{13}$, $130_{14}$, multiple server computers $150_3$, $150_4$, and multiple server audio stations $150_5$, $150_6$, and multiple packet based networks $140_3$, $140_4$ through a traffic management device 810. It should be appreciated that exemplary audio stations $130_7$, $130_8$, $130_9$, $130_{10}$, $130_{11}$, $130_{12}$, $130_{13}$, $130_{14}$, exemplary server computers $150_3$, $150_4$, and exemplary packet based networks $140_3$, $140_4$ are implemented in similar manners to audio station(s) 130, server computer 150, and packet based network 140, respectively (discussed above in connection with FIG. 1), and exemplary server audio stations $150_5$, $150_6$, are implemented in a similar manner to server computer 150 (with suitable software and/or hardware modifications to perform the relevant operations discussed herein).

When the number of networked devices increases, the amount of network traffic also increases. To increase efficiencies, the network is broken into smaller segments and the segments are interconnected using intelligent devices that manage the traffic between the segments. To this end, the traffic management device 810 suitably includes bridges, switches, routers, and other known devices. In a manner that is well known, the traffic management device dynamically "learns" the addresses of the devices on each network segment and manages communications between the network segments.

Figure 8:
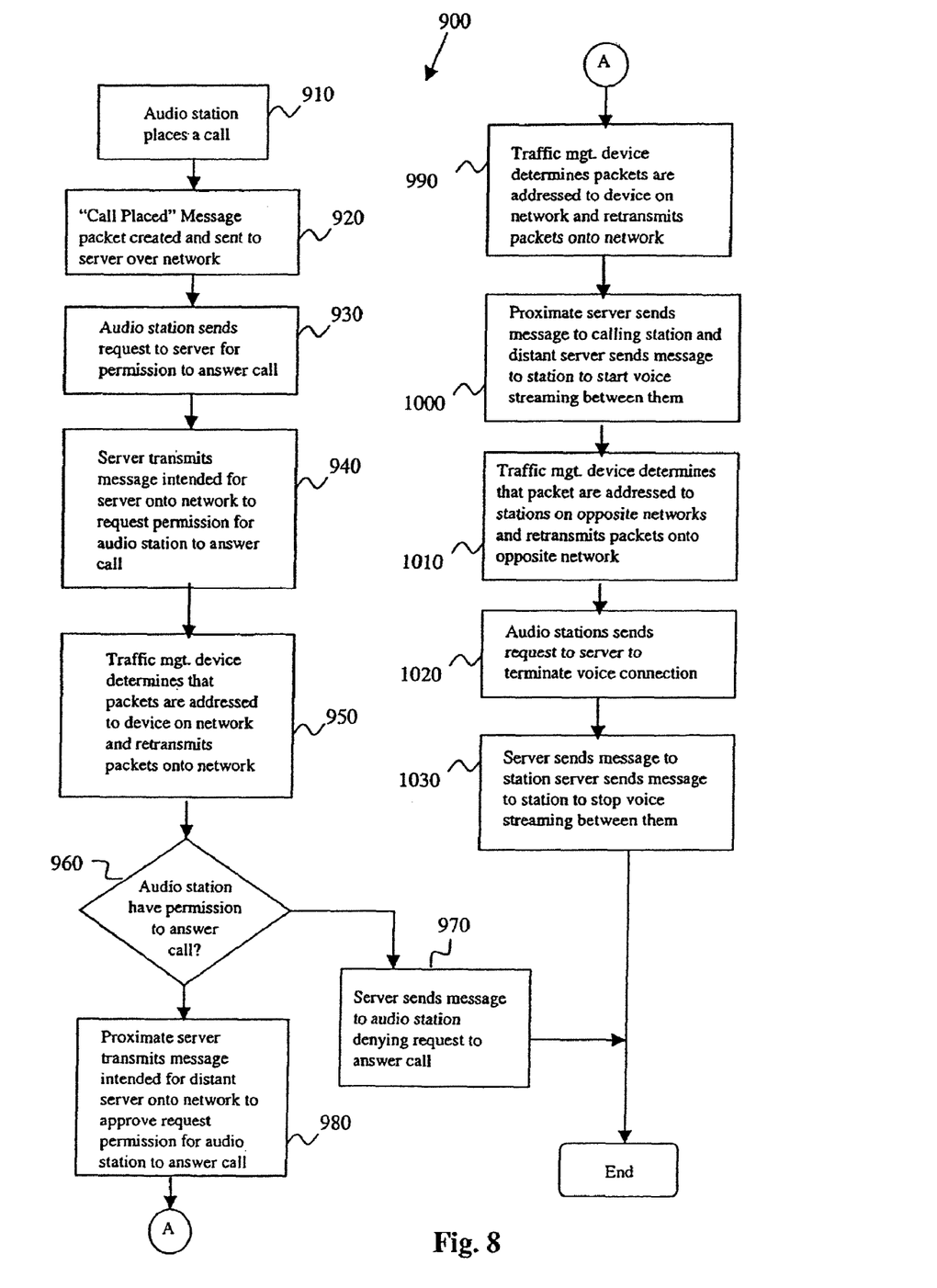
FIG. 8 is an illustrative flow diagram describing a process for voice over packet communication in the system illustrated in FIG. 7.

FIG. 8 is an illustrative flow diagram describing a process 900 for voice over packet communication in the system illustrated in FIG. 7. In general, the traffic management devices look at the source and destination of each packet transmitted on the network to determine if the packet is destined for a device on a segment different than the source. If so, the traffic management device retransmits the packet onto the appropriate network segment. This method reduces traffic on each segment to only packets transmitted or received by devices on that segment.

More particularly, at step 910 a user places a call (i.e., seeks to initiate an audio connection) through one of the audio stations (audio station $130_7$, for example). At step 920, the calling audio station sends a message to the server computer that is on its network segment (in this example, the message is sent to server computer $150_3$ over packet based network $140_3$) indicating that the calling audio station has requested an audio connection, and that server computer sends message(s) over the network indicating that the calling audio station has placed the call. Further, the traffic management device relays the indication that the calling audio station has requested an audio connection to the distant network segment (in this example, packet based network $140_4$). At step 930, a user at a distant audio station (in this example, audio station $130_{13}$) indicates a request to answer the call. Accordingly, the distant audio station sends a request for permission to answer the call to the server computer on its network segment (in this example, to server computer $150_4$ over packet based network $140_4$). At step 940, the server computer on the network segment that is distant from the caller (i.e., server computer $150_4$ in this example) transmits the request for permission to answer the call over its respective network segment.

At step 950, the traffic management device 810 determines that the message packets indicating the request for permission to answer the call are addressed to the server computer that is on the same network segment as the caller, and, accordingly, the traffic management device relays the packets onto the network segment of the caller. At step 960, the server computer on the network segment of the caller (i.e., the "proximate server") determines whether the distant audio station that has requested permission to answer the call should have permission to answer the call. If so, then the proximate server computer proceeds to step 980; otherwise, the proximate server computer sends a message to the distant audio station that has requested the permission indicating that the request to answer the call is denied (step 970) and the remaining steps are bypassed.

At step 980, the proximate server computer transmits a message onto its network segment indicating approval of the distant audio station's request for permission to answer the call. At step 990, the traffic management device 810 determines that the packets transmitted by the proximate server computer (step 980) are addressed to a device on the distant network segment and, accordingly, relays the packets to the distant segment.

At step 1000, the proximate server computer sends a message to the audio station that initiated the call and the distant server computer sends a message to the audio station that has requested permission to receive the call, and in response these two audio stations begin transmitting voice data packets between them. At step 1010, the traffic management device 810 determines that the streaming packets are addressed to audio stations on different network segments and relays the packets between the segments as appropriate. The audio stations sound the corresponding audio on their speakers.

At step 1020, the user who answered the call inputs a request to terminate the audio connection (or to "hang up") into the server computer on its network segment. The request to end the call may include an active request (such as, for example, actuation of a "call end" button), and in alternative embodiments may in addition or alternatively include a passive request (such as, for example, a locating and tracking detection that the user has left a proximity of the server computer from which the user answered the call). At step 1030, the proximate server computer sends a message to the audio station that initiated the call and the distant server computer sends a message to the audio station that received the call, and in response the two audio stations stop transmitting voice data packets between them.

Figure 9:
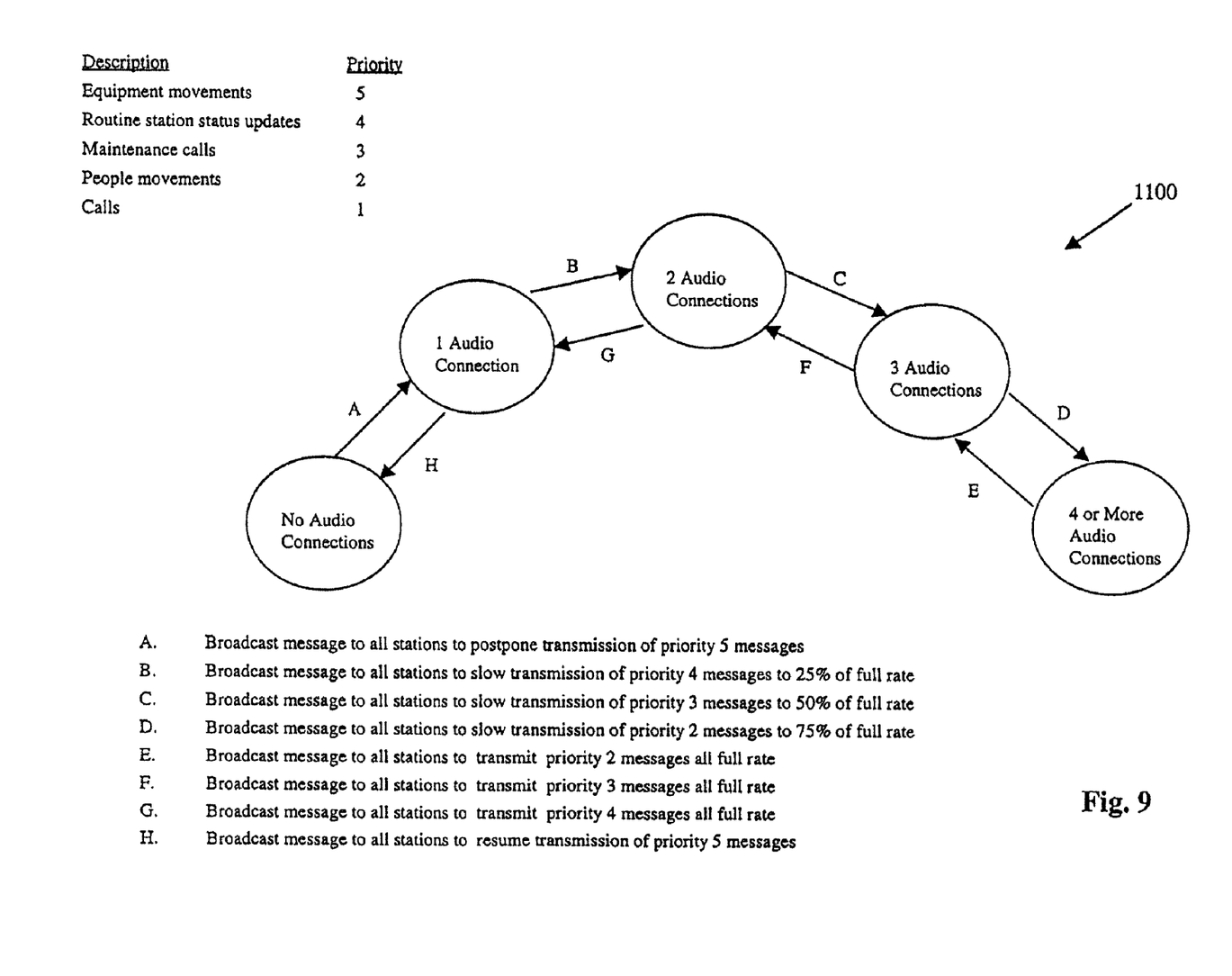
FIG. 9 describes an illustrative prioritization scheme used to improve quality of service.

Next, FIG. 9 shows an illustrative prioritization scheme 1100 for improving quality of service (i.e., "voice quality," or "QOS"). When transmitting voice over a packet network, increased bandwidth for the duration of the audio connection is one way to ensure good quality, real-time voice communication. Most telephony systems have historically dedicated a channel for each voice connection in order to guarantee bandwidth. However, when sending voice in packets over an asynchronous network, guaranteeing bandwidth is much more difficult. This is especially true when the network is also supporting numerous other voice and data applications.

Several methods have been employed to deal with the problem of voice quality of service. One solution has been to move to higher speed networks. Another is to design networks that provide multiple paths through which packets can travel. Yet another is to use routers and switches that provide quality of service features. Devices with these features are able to recognize the type of each packet it is processing. These devices can then give voice packets a priority over other packet types so that they are processed sooner. Illustratively, some routers and switches will purposely introduce delays in the processing of lower priority packets to cause the sending devices to slow the rate at which packets are sent. This reduces the amount of bandwidth used by low priority traffic.

As shown in FIG. 9, a server computer categorizes the types of traffic on the network into levels of priority to be postponed and/or throttled back to free bandwidth for voice traffic depending on the priority level and then number of simultaneous voice connections. If a voice connection is established, low priority traffic such as messages related to changes in the location of equipment, is postponed until the voice connection is terminated. If two voice connections are established, both the lowest priority and second from lowest priority traffic is postponed.

More particularly, the exemplary embodiment includes five priority levels (where "1" indicates the highest and "5" indicates the lowest priority), as follows:

| Priority | Information/Data Type |
|---|---|
| 1 | calls |
| 2 | people movements/tracking |
| 3 | maintenance |
| 4 | routine status updates |
| 5 | equipment movements/tracking |

Referring still to FIG. 9, when one or more audio connections are established, the server computer(s) instruct all audio stations to postpone transmission of priority 5 (equipment movements/tracking) messages; otherwise, the server computer(s) instruct all audio stations to allow transmission of priority 5 messages.

Additionally, when two or more audio connections are established, the server computer(s) instruct all audio stations to slow transmission of priority 4 (routine status updates) messages to 25% of the full rate; otherwise, the server computer(s) instruct all audio stations to allow transmission of priority 4 messages at the full rate.

Additionally, when three or more audio connections are established, the server computer(s) instruct all audio stations to slow transmission of priority 3 (maintenance) messages to 50% of the full rate; otherwise, the server computer(s) instruct all audio stations to allow transmission of priority 3 messages at the full rate.

Additionally, when four or more audio connections are established, the server computer(s) instruct all audio stations to slow transmission of priority 2 (people movements/tracking) messages to 75% of the full rate; otherwise, the server computer(s) instruct all audio stations to allow transmission of priority 2 messages at the full rate.

Figure 10:
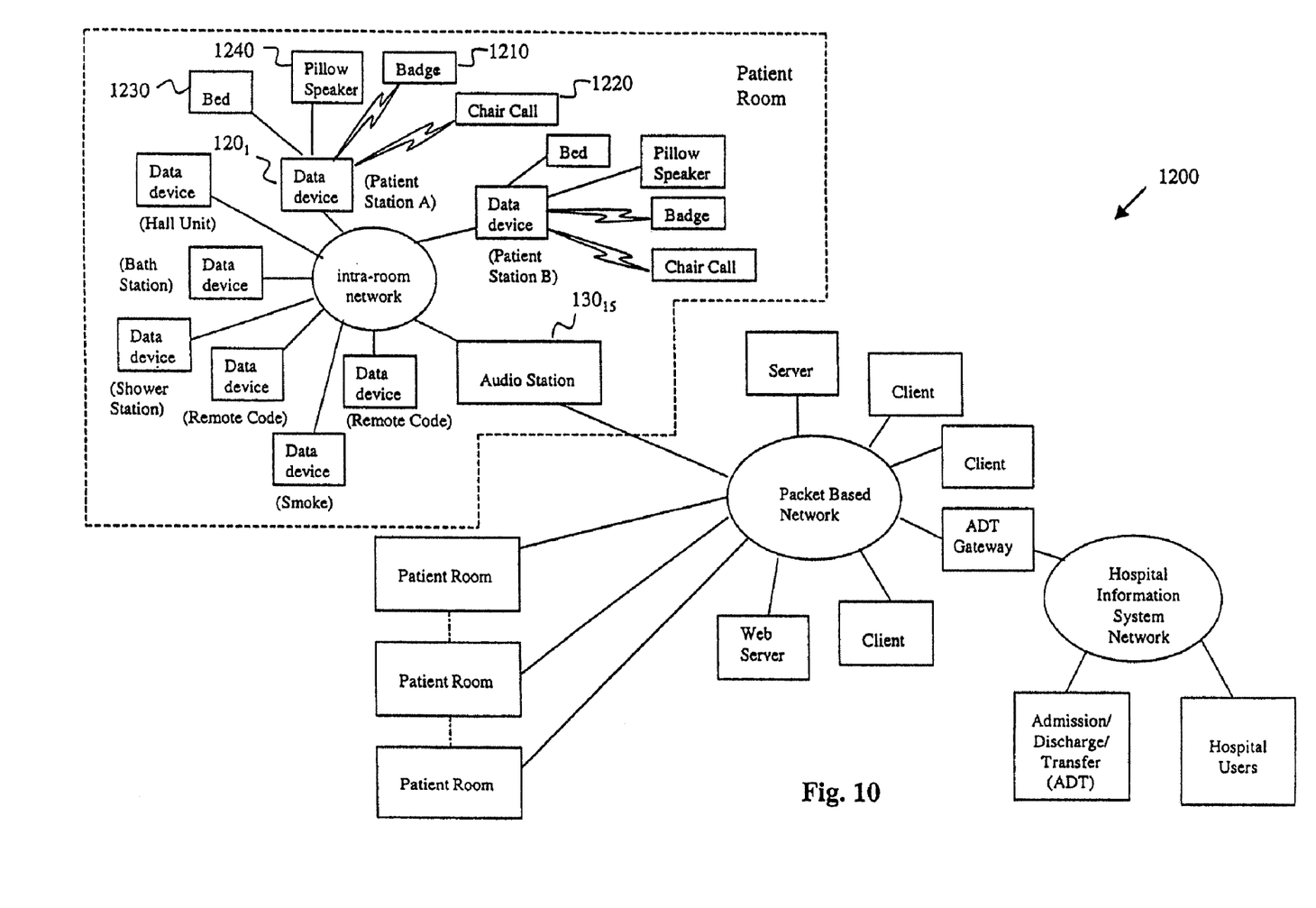
FIG. 10 illustrates an arrangement in which various signaling equipment is coupled to data devices within the system architecture of FIG. 1.

Next, FIG. 10 illustrates an arrangement 1200 in which various signaling equipment is coupled to data devices within the system architecture of FIG. 1. For example, locating and tracking systems that track movement of caregivers and equipment through hospital facilities are known. Some such systems include badges that use infrared, radio frequency, ultrasonic, or other types of transmitters that periodically transmit identification signals. In operation, receivers throughout the facility (not shown) suitably detect the identification information. It is noted that locating and tracking inputs for the present invention may be implemented with a COMposer® system or a COMLNX™ system (available from Hill-Rom NetLinx located in Cary, N.C.) or similar system. Further, as illustrated in FIG. 10, one or more data devices $120_1$ may be configured to receive identification signals from locating and tracking badges 1210, and may be further configured to receive information signals from various other signaling equipment such as chair call devices 1220, pillow speakers 1240, and/or a hospital bed status unit 1230. U.S. Pat. Nos. 5,561,412; 5,699,038; and 5,838,223 (which have been incorporated herein by reference) disclose the operation of such equipment and, furthermore, suitable alternative signaling equipment is known. Additionally, it is noted that audio station(s) $130_{1-5}$ may be combined or otherwise integrated with the respective data device(s) $120_1$ and/or any suitable number of the various signaling devices.

In an illustrated embodiment of the present invention, a hospital bed is provided with an audio station 130 to communicate with the network 140. In this embodiment, the hospital bed itself includes a computer and provides audio station 130 for communicating voice data and other non-voice from the hospital bed to the network. In another embodiment of the present invention, the audio station 130 is provided on a cart or other device which moves with the patient through the hospital to provide a patient point of care computer system. Embodiments of a computer system on a bed or cart are included in U.S. patent application Ser. No. 09/849,580, filed May 4, 2001 and U.S. Ser. No. 60/310,092, filed Aug. 3, 2001, the disclosures of which are expressly incorporated by reference herein.

By providing the audio station 130 on the hospital bed or cart, the system of the present invention provides network communication from the area around the patient point of care to the hospital information network 190 at all times. In other words, when the hospital bed is moved from room to room, a network connection is made between the audio station 130 on the hospital bed and the network 140. Likewise, when the patient care cart moves with a patient through the facility, communication between the audio station 130 on the patient care cart and the network 140 is made. Such communication is accomplished through a wired connection or a wireless data connection within the hospital. Therefore, the patient and caregiver have improved data and voice communication over the network at the patient point of care. Caregivers have access to patient data including video information, and voice communication from a remote location to the patient's bedside. Therefore, caregivers can access patient chart information, test results, etc. from a remote location.

Some of the data devices 120 are illustratively physiological monitors, treatment devices, and therapy devices. A network computer in the room, on the bed, or on a patient cart is coupled to the data device by an RS-232 port or other suitable connector. The computer processes signals from the monitors, treatment devices, and therapy devices on a real time basis. The monitors, treatment devices, and therapy devices include, but are not limited to, heart rate monitors, temperature sensors, blood pressure monitors (invasive and noninvasive), EKG monitors, blood oxygen sensors, capnographs, ventilators, IV pumps, scales, and chest drainage monitors. Additional details of the computer and data devices are disclosed in U.S. patent application Ser. No. 09/849,580, filed May 4, 2001, and U.S. patent application Ser. No. 60/310,092, filed on Aug. 3, 2001, the disclosures of which are incorporated herein by reference.

In another illustrated embodiment, the computer on the bed or cart is used to provide a medication scan, TV, phone, and bed controls, internet access, e-mail, music or DVD players, and nurse call. Computer is also coupled to a display. Illustratively, display 24 is a touch screen display which can be used as both a TV terminal and a computer display. Software provides a keyboard emulation on display to permit a user to input information to computer using touch screen display. It is understood that any conventional input device such as a pen or stylus based input, a keyboard, a mouse, a joy stick, a voice recognition input, or other suitable input device may be used to input information into computer.

Although the invention has been described in detail with reference to certain illustrated embodiments, variations and modifications exist within the scope and spirit of the present invention as defined in the following claims.

The invention claimed is:

1. A healthcare computer system comprising
a first computer device located in a patient room,
a first plurality of data devices communicatively coupled to the first computer device, at least one of the plurality of data devices comprising a vital signs monitor,
a first hospital bed communicatively coupled to the first computer device, and
a packet based network, the first computer device being configured to send data from the first plurality of data devices and from the first hospital bed as message packets via the packet based network for receipt by a third computer device which is coupled to the packet based network.

2. The healthcare computer system of claim 1, wherein the first computer device has audio communication capability.

3. The healthcare computer system of claim 2, wherein the first computer device comprises an audio station that comprises a microphone, a speaker and a digital-to-analog converter to provide at least part of the audio communication capability.

4. The healthcare computer system of claim 1, wherein at least another one of the first plurality of data devices comprises one of an IV pump, a ventilator, a defibrillator, and a compression boot.

5. The healthcare computer system of claim 1, further comprising a second computer device, a second plurality of data devices communicatively coupled to the second computer device, and a second hospital bed communicatively coupled to the second computer device.

6. The healthcare computer system of claim 5, wherein the first hospital bed, the second hospital bed, the first plurality of data devices and the second plurality of data devices are located in the patient room.

7. The healthcare computer system of claim 1, further comprising a second plurality of data devices communicatively coupled to the first computer device and a second hospital bed communicatively coupled to the first computer device.

8. The healthcare computer system of claim 1, wherein the packet base network comprises a server configured to manage communication of message packets from the first computer device to the third computer device by prioritizing the message packets from the first computer device.

9. The healthcare computer system of claim 8, wherein the server delays sending message packets associated with a lower priority until processing of packets with a higher priority is complete.

10. The healthcare computer system of claim 9, wherein message packets containing voice data are associated with a highest priority.

11. The healthcare computer system of claim 1, further comprising a transmitter to be carried by a caregiver and a receiver configured to receive a signal from the transmitter and to transmit at least one identification packet to the third computer device.

12. The healthcare computer system of claim 1, wherein the first computer device is mounted to the first hospital bed.

13. The healthcare computer system of claim 12, wherein the first computer device is configured to serve as an audio station on the first hospital bed.

14. The healthcare computer system of claim 1, further comprising an Admission/Discharge/Transfer (ADT) system having an ADT computer configured to transmit ADT data packets to the first computer device.

15. The healthcare computer system of claim 1, further comprising an Admission/Discharge/Transfer (ADT) system and the third computer device is included in the ADT system.

16. The healthcare computer system of claim 1, further comprising a nurse call system having a nurse call computer configured to transmit audio packets to the first computer device.

17. The healthcare computer system of claim 1, further comprising a nurse call system and the third computer device is included in the nurse call system.

18. The healthcare computer system of claim 1, wherein the third computer device is located in another patient room.

19. The healthcare computer system of claim 18, wherein the first computer device is configured to send voice packets to the third computer device.

20. The healthcare computer system of claim 1, wherein at least one of the data devices of the first plurality of data devices comprises an input device to input data and instructions concerning a patient.

* * * * *